US00PP19961P2

(12) United States Plant Patent
Klemm

(10) Patent No.: US PP19,961 P2
(45) Date of Patent: Apr. 28, 2009

(54) ***HELIOTROPIUM* PLANT NAMED 'KLEHA07520'**

(50) Latin Name: *Heliotropium arborescens*
Varietal Denomination: KLEHA07520

(75) Inventor: Nils Klemm, Stuttgart (DE)

(73) Assignee: Klemm + Sohn GmbH & Co. KG, Stuttgart (DE)

( * ) Notice: Subject to any disclaimer, the term of this patent is extended or adjusted under 35 U.S.C. 154(b) by 0 days.

(21) Appl. No.: 12/079,192

(22) Filed: Mar. 25, 2008

(51) Int. Cl.
*A01H 5/00* (2006.01)

(52) U.S. Cl. ..... Plt./438

(58) Field of Classification Search ..... Plt./438
See application file for complete search history.

*Primary Examiner*—Annette H Para
(74) *Attorney, Agent, or Firm*—Jondle & Associates, P.C.

(57) ABSTRACT

A new cultivar of *Heliotropium* particularly characterized by purple-blue flowers, a medium/compact growth habit and flowers with a vanilla-hyacinth-like fragrance, is disclosed.

1 Drawing Sheet

Genus and species: *Heliotropium arborescens.*
Variety denomination: 'KLEHA07520'.

BACKGROUND OF THE NEW PLANT

The present invention comprises a new and distinct cultivar of *Heliotropium,* botanically known as *Heliotropium arborescens,* and hereinafter referred to by the cultivar name 'KLEHA07520'. 'KLEHA07520' was discovered as a seedling resulting from a cross in summer 2003 in Stuttgart, Germany between the proprietary female *Heliotropium* parent, 'V 018' (unpatented) and the male parent, an unnamed typical individual plant of *Heliotropium* (unpatented). A single plant selection was subsequently chosen for further evaluation and for asexual propagation.

The new cultivar was created in 2003 in Stuttgart, Germany and has been asexually reproduced repeatedly by vegetative cuttings in Stuttgart, Germany over a three and one-half-year period. 'KLEHA07520' has been found to retain its distinctive characteristics through successive asexual propagations.

Plant Breeder's Rights for this cultivar were applied for in Canada on Apr. 11, 2007. 'KLEHA07520' has not been made publicly available more than one year prior to the filing date of this application.

SUMMARY OF THE INVENTION

The following are the most outstanding and distinguishing characteristics of this new cultivar when grown under normal commercial practices in a greenhouse in Stuttgart, Germany.

1. Purple-blue flowers;
2. A medium/compact growth habit; and
3. Flowers with a vanilla-hyacinth-like fragrance.

DESCRIPTION OF THE PHOTOGRAPHS

This new *Heliotropium* plant is illustrated by the accompanying photographs which show blooms, buds, and foliage of the plant; the colors shown are as true as can be reasonably obtained by conventional photographic procedures. The photographs are of plants about 4-months old and grown from rooted cuttings in a 12-cm pot under greenhouse (glasshouse) in Stuttgart, Germany under conditions which approximate those generally used in commercial practice.

DESCRIPTION OF THE NEW CULTIVAR

Figure 1:
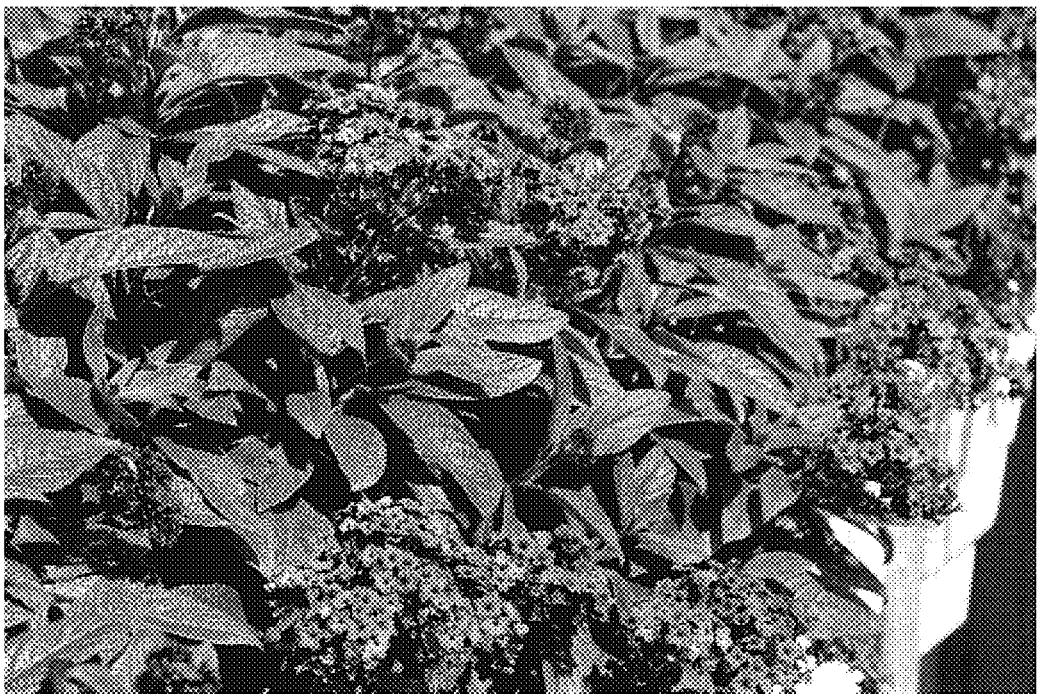
FIG. 1 shows the whole plant habit, including blooms, buds and foliage.
Figure 2:
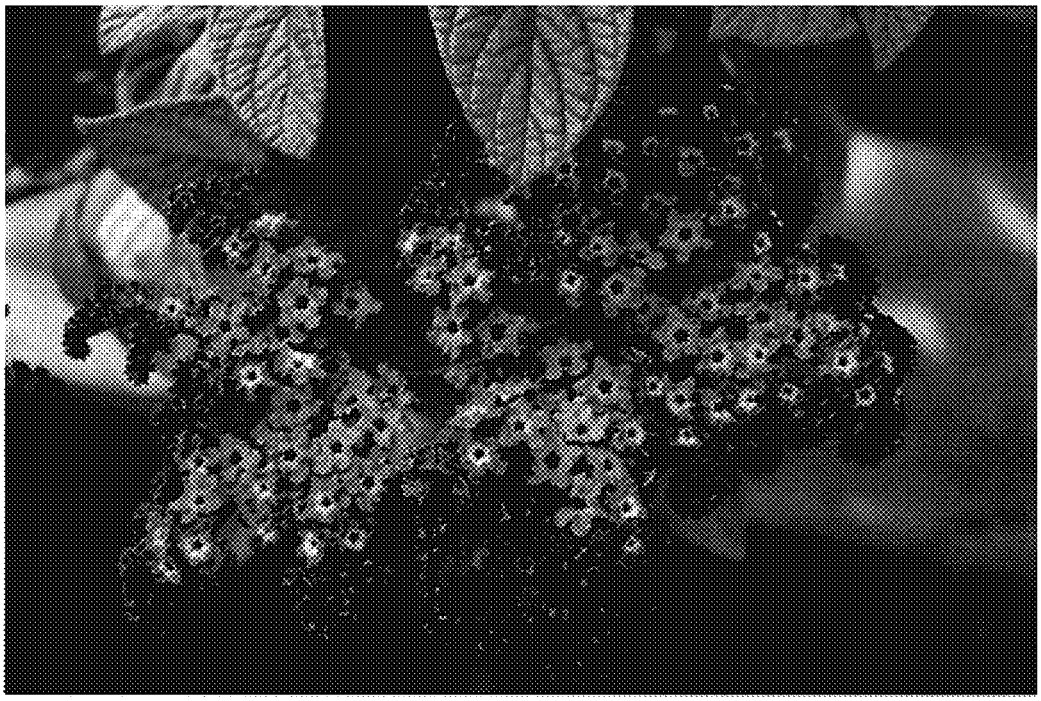
FIG. 2 shows a close-up of the mature flowers.

The following detailed descriptions set forth the distinctive characteristics of 'KLEHA07520'. The data which define these characteristics were collected from asexual reproductions carried out in Stuttgart, Germany. The plant history was taken on 3-month old plants in 12-cm pots that were pinched once approximately 6 days after planting and grown in a greenhouse in February through April. The color readings were determined under natural light. Color references are to the R.H.S. Colour Chart of The Royal Horticultural Society of London (R.H.S.) (2001).

DESCRIPTION OF THE NEW PLANT

Classification:
- *Family.*—Boraginaceae.
- *Genus and species.*—*Heliotropium arborescens.*
- *Common.*—Heliotrope.

Parentage:
- *Female parent.*—The proprietary *Heliotropium* plant 'V 018' (unpatented).
- *Male parent.*—An unnamed typical individual plant of *Heliotropium* (unpatented).

Plant:
- *Form.*—Rounded, bushy.
- *Growth habit.*—Upright.
- *Height from soil level to top of plant plane.*—30.0 cm.
- *Diameter* (*area of spread*).—28.0 cm.
- *Time to initiate roots.*—6 to 8 days.
- *Time to produce a rooted cutting.*—16 to 18 days.
- *Root description and habit.*—Dense, freely branching, white, medium-thickness and fibrous texture.
- *Time to produce a finished plant.*—About 70 days.

Branches:
- *Type.*—Lateral flowering branches.

*Quantity per plant.*—4 to 5.
*Length.*—About 15.0 cm.
*Diameter.*—12.0 cm.
*Internode length.*—4.0 cm.
*Texture.*—Rough.
*Color.*—RHS 137A.

Leaves:
*Arrangement and type.*—Alternate.
*Quantity per branch.*—10.
*Shape.*—Elliptical.
*Apex.*—Rounded.
*Base.*—Attenuate.
*Margin.*—Entire.
*Venation pattern.*—Pinnate.
*Venation color.*—RHS 137D.
*Length.*—2.0 cm to 3.0 cm.
*Width.*—0.8 cm to 1.5 cm.
*Texture* (*both for the upper and lower surfaces*).—Rough.
*Color.*—Upper surface (both immature and mature): RHS 137A. Lower surface (both immature and mature): RHS 137C.
*Petiole.*—Length: 0.5 cm to 2.0 cm. Diameter: 0.1 cm to 0.15 cm. Texture: Rough. Color RHS 137C.

Bud:
*Shape/size.*—Elliptical, small.
*Apex.*—Acute.
*Length.*—0.3 cm.
*Diameter.*—0.1 cm.
*Color.*—RHS 137C.

Inflorescence:
*Type.*—Terminal compound cymes.
*Height.*—1.5 cm to 5.0 cm.
*Width.*—3.0 cm to 12.0 cm.
*Quantity of open flowers per inflorescence.*—5 to 50.
*Fragrance.*—Vanilla-hyacinth-like.
*Lastingness of inflorescence on the plant.*—About 10 days.
*Flowering season.*—Spring to fall.
*Peduncle.*—Strength: Medium. Aspect: Inward-curved. Length: Variable. Diameter: 0.1 cm to 0.2 cm. Texture: Rough. Color: RHS 137D.

Flowers:
*Type.*—Funnelform.
*Length.*—0.4 cm to 0.5 cm.
*Petals.*—Quantity: 5 per flower. Apex: Rounded. Base: Attenuate. Margin: Entire. Texture (for both surfaces): Smooth. Color, when first open, for both upper and lower surfaces: RHS 92C. Color, when fully open, for both upper and lower surfaces: RHS 92C.
*Corolla tube.*—Present but too small to take any quantitative measurements and colors.
*Calyx.*—Diameter: 0.1 cm.
*Sepals.*—Quantity: 5. Shape: Ovate. Length: 0.4 cm. Width: 0.1 cm. Apex: Acute. Margin: Entire. Texture (of both surfaces): Smooth. Color (of both surfaces): RHS 137C.

Reproductive organs: Unable to determine reproductive organs due to small size.
Fruit and seed set: None observed.
Disease and insect resistance: Not observed.

COMPARISON WITH PARENTAL AND COMMERCIAL CULTIVARS

'KLEHA07520' differs from the female parent, the proprietary *Heliotropium* 'V 018' (unpatented) in that 'KLEHA07520' has purple-blue flowers, medium to dark-green leaves and a medium/compact growth habit, while 'V 018' has lavender-blue flowers, medium green leaves and a medium/strong growth habit.

'KLEHA07520' differs from the commercial comparison variety 'Marino Compact' (unpatented) in that 'KLEHA07520' has purple-blue flowers, a medium/compact growth habit and medium to dark-green leaves, while 'Marino Compact' has dark lavender-blue flowers, a compact growth habit and green leaves.

I claim:

1. A new and distinct cultivar of *Heliotropium* plant as shown and described herein.

* * * * *